(12) United States Patent
Zhang et al.

(10) Patent No.: US 11,911,124 B2
(45) Date of Patent: Feb. 27, 2024

(54) ACTIVE-PASSIVE PARALLEL-CONNECTED REDUCTION ROBOT

(71) Applicant: THE FIRST MEDICAL CENTER OF PEOPLE'S LIBERATION ARMY GENERAL HOSPITAL, Beijing (CN)

(72) Inventors: Lihai Zhang, Beijing (CN); Wen Zhao, Beijing (CN); Lei Hu, Beijing (CN); Hailong Du, Beijing (CN)

(73) Assignee: THE FIRST MEDICAL CENTER OF PEOPLE'S LIBERATION ARMY GENERAL HOSPITAL, Beijing (CN)

( * ) Notice: Subject to any disclaimer, the term of this patent is extended or adjusted under 35 U.S.C. 154(b) by 0 days.

(21) Appl. No.: 18/369,150

(22) Filed: Sep. 16, 2023

(65) Prior Publication Data

US 2024/0000531 A1 Jan. 4, 2024

Related U.S. Application Data

(63) Continuation of application No. PCT/CN2021/115607, filed on Aug. 31, 2021.

(30) Foreign Application Priority Data

Mar. 16, 2021 (CN) .......................... 202110278937.5

(51) Int. Cl.
 *A61B 34/37* (2016.01)
 *B25J 17/02* (2006.01)
 *A61B 34/00* (2016.01)

(52) U.S. Cl.
 CPC .............. *A61B 34/37* (2016.02); *A61B 34/70* (2016.02); *B25J 17/0258* (2013.01)

(58) Field of Classification Search
 CPC ................ A61B 17/6433; A61B 17/66; A61B 2017/00398; A61B 2034/304;
 (Continued)

(56) References Cited

U.S. PATENT DOCUMENTS

2013/0190774 A1 7/2013 Beira et al.

FOREIGN PATENT DOCUMENTS

CN 102670309 A 9/2012
CN 206414336 U 8/2017
(Continued)

OTHER PUBLICATIONS

International Search Report of PCT Patent Application No. PCT/CN2021/115607 dated Dec. 20, 2021.
(Continued)

*Primary Examiner* — Scott Luan

(57) ABSTRACT

An active-passive parallel-connected reduction robot includes: an active manipulator, provided with an active output end having multiple degrees of freedom; a synchronized motion platform, a fracture reduction needle being fixedly mounted on the synchronized motion platform, the active output end of the active manipulator being connected to the synchronized motion platform; and a passive manipulator, one end thereof being fixedly provided, the other end being provided with a passive output end having multiple degrees of freedom, and the passive output end being slidably mounted on the synchronized motion platform. The passive manipulator is capable of maintaining a locked degree of freedom when the active manipulator drives the synchronized motion platform to insert the fracture reduction needle into a fractured end requiring reduction. The active manipulator drives the synchronized motion platform to execute a reduction operation with the support of the passive manipulator.

10 Claims, 4 Drawing Sheets

(58) Field of Classification Search
CPC ......... A61B 34/30; A61B 50/13; A61B 34/37; A61B 34/70; B25J 17/0258
See application file for complete search history.

(56) References Cited

FOREIGN PATENT DOCUMENTS

| | | |
|---|---|---|
| CN | 107928956 A | 4/2018 |
| CN | 109330686 A | 2/2019 |
| CN | 112957130 A | 6/2021 |
| WO | 2017020081 A1 | 2/2017 |

OTHER PUBLICATIONS

Written Opinion of the International Searching Authority of PCT Patent Application No. PCT/CN2021/115607 dated Dec. 20, 2021.

ACTIVE-PASSIVE PARALLEL-CONNECTED REDUCTION ROBOT

CROSS REFERENCE TO RELATED APPLICATIONS

The present application is a Continuation Application of PCT Application No. PCT/CN2021/115607 filed on Aug. 31, 2021, which claims the benefit of Chinese Patent Application No. 202110278937.5 filed on Mar. 16, 2021. All the above are hereby incorporated by reference in their entirety.

TECHNICAL FIELD

The invention relates to the technical field of medical equipment, in particular to an active-passive parallel-connected reduction robot.

BACKGROUND

Fracture reduction operation is a key link in bone therapy. Because there are complex and powerful soft tissues of muscle around the fracture, the reduction operation requires strong reduction force and dexterous reduction operation. At the same time, due to the limited operating space, the occupation space and movement space of the reset mechanism cannot occupy the space of the surgeon and the patient.

In order to complete the dexterous and large-load movement of the traditional reset mechanism, the surgical robot needs to realize multi-degree-of-freedom spatial movement. The structure and assembly are relatively complicated, and it is often bulky, requiring more space for installation and arrangement, and more space of surgeon is occupied, which is not conducive to the doctor's operation, and cannot meet the clinical needs.

In view of this, the present invention is proposed.

SUMMARY

The purpose of the present invention is how to solve the problem of complex assembly and large space occupation of fracture reduction robot, and provide a simple structure, small volume, and reliable active-passive parallel-connected reduction robot.

In order to realize the above-mentioned purpose of the invention, the present invention provides the following technical solutions.

An active-passive parallel-connected reduction robot includes:
  an active manipulator provided with an active output of multiple degrees of freedom;
  a synchronized motion platform, on which a fracture reduction needle is fixedly installed, and the active output end of the active manipulator is connected to the synchronized motion platform; and a passive manipulator, of which one end is fixed, and the other end including a one end of multiple degrees of freedom, and the passive output end is slidably installed on the synchronized motion platform;
  the passive manipulator keeps degrees of freedom locked in response to the active manipulator drives the synchronized motion platform to insert the fracture reduction needle into a fracture end requiring reduction, and the active manipulator drives the synchronized motion platform to perform a reduction operation under the support of the passive manipulator.

In some embodiments, the synchronized motion platform includes:
  a platform main body including a robot-end moving platform connected with the active manipulator and a parallel transmission mechanism connected with the robot-end moving platform for parallel transmission of power;
  a uniform strengthening wrist configured to fixedly install the fracture reduction needle, and the uniform strengthening wrist is fixedly connected with the parallel transmission mechanism of the platform main body In some embodiments, the parallel transmission mechanism includes first parallel transmission mechanism that performs a parallel motion on a first plane and a second parallel transmission mechanism that performs parallel motion on a second plane, the first plane intersects the second plane.

In some embodiments, the parallel transmission mechanism includes a follow-up end platform fixedly connected with the uniform strengthening wrist; the first parallel transmission mechanism includes a first support rod and a second support rod parallel to the first support rod, a first rotation shaft and a second rotation shaft parallel to the first rotation shaft, and both ends of the first support rod are respectively fixedly connected to a first parallel hinge seat and a second parallel hinge seat, one end of the first rotation shaft is fixedly connected to the robot-end moving platform, and the other end of the first rotation shaft is rotatably connected to the first parallel hinge seat; one end of the second rotation shaft is fixedly connected to the follow-up end platform, and the other end of the second rotation shaft is rotatably connected to the second parallel hinge seat;

the second parallel mechanism includes a third support rod parallel to the second support rod, a fourth rotation shaft and a fifth rotation shaft parallel to the fourth rotation shaft; both ends of the second support rod are respectively fixedly connected to a third parallel hinge seat and a fourth parallel hinge seat; both ends of the third support rod are respectively fixedly connected to a fifth parallel hinge seat and a sixth parallel hinge seat; the fourth rotation shaft rotatably passes through the robot-end moving platform, and both ends of the fourth rotation shaft are rotatably installed on the third parallel hinge seat and the fifth parallel hinge seat respectively; the fifth rotation shaft rotatably passes through the follow-up end platform, and both ends of the fifth rotation shaft are respectively rotatably installed on the fourth parallel hinge seat, and the sixth parallel hinge seat.

In some embodiments, the robot-end moving platform includes a platform body and a first connecting block and a second connecting block fixedly connected to the platform body; one end of the first rotation shaft is fixedly connected with the first connecting block; the fourth rotation shaft rotatably passes through the second connecting block.

In some embodiments, the follow-up end platform includes a cross arm and a vertical arm fixedly connected with the cross arm; the second rotation shaft is fixedly connected to the vertical arm, the fifth rotation shaft rotatably passes through the cross arm.

In some embodiments, the synchronized motion platform includes a spherical hinge slidably arranged on the second support rod, and the passive output end of the passive manipulator is connected to the spherical hinge.

In some embodiments, the uniform strengthening wrist includes a bracket, a motor, a motor output shaft screw, a sliding shaft, a stress adjustment rod, a universal locking buckle, a sliding shaft fixed plate and a universal locking bayonet fixed shaft;

wherein the motor is fixed on the bracket, the motor output shaft screw is fixed on the motor output shaft, the motor output shaft screw and the sliding-shaft fixing plate are screw driven; a rotation of the motor drives the sliding-shaft fixing plate to move up and down; the sliding shaft is fixedly connected with the sliding-shaft fixing plate; the stress adjustment rod is fixedly connected with the bracket; one end of the universal locking buckle is connected with the fracture reduction needle, and the other end of the universal locking buckle is fixed with the stress adjustment rod or the universal locking bayonet fixed shaft;

in response to the fracture reduction needle being inserted into the fracture reduction end, the universal locking buckle fixes the fracture reduction needle and a racket section together; the motor rotates to drive the sliding shaft fixed plate to move up and down to adjust arm of force of the stress adjustment rod and the bracket.

In some embodiments, the active output end of the active manipulator is an end-connection flange with six degrees of freedom in space.

In some embodiments, the passive manipulator includes a first moving member, a second moving member connected to the first moving member through a first spherical hinge, and a third moving member rotatably connected to the second moving member through a rotary hinge, a fourth moving member connected to the third moving member through a second spherical hinge, and a locking member for locking the first spherical hinge, the rotary hinge, and the second spherical hinge.

Compared with prior art, the beneficial effect of the present invention is as following.

The present invention proposes an active-passive parallel-connected reduction robot structure: the parallel mechanism of the active manipulator and the passive manipulator is adopted, the passive manipulator with small volume and large load is arranged in the operation space, and the large-rigidity support is used to assist the robot to complete the output of large force load. The active manipulator completes large power and dexterous movement, and with the support of the passive branch chain, the power demand of the active manipulator is reduced; the synchronized motion platform outputs the movement of the active manipulator in a crowbar mode, and completes the large-load dexterous reduction operation. Therefore, the active-passive and parallel-connected reduction robot structure of the present invention realizes the fracture reduction operation through the active manipulator, the passive manipulator and the synchronized motion platform, and is simple, stable, reliable, easy for assemble and unassembled, has a small footprint, and facilitates a surgeon in performing surgical operations.

Figure 1:
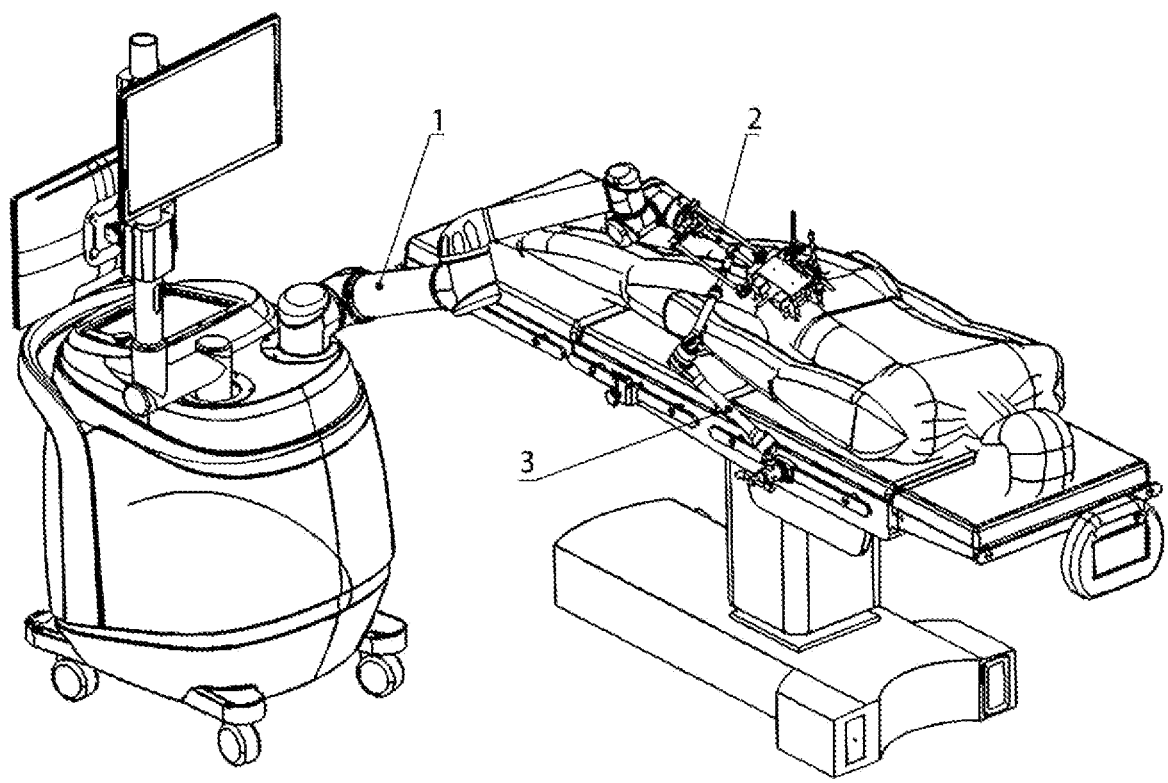
FIG. 1 is a schematic diagram of the use state of the active-passive parallel-connected reduction robot of the present invention.

Explanation of the symbols in the accompanying drawings: 1-active manipulator; 101-end-connection flange; 2-synchronized motion platform; 200-platform main body; 201-robot-end moving platform; 202-first parallel hinge seat; 203-first support rod; 204-fourth rotation shaft; 205-second support rod; 206-fifth parallel hinge seat; 207-third support rod; 208-follow-up end platform; 209-fifth rotation shaft; 2010-second rotation shaft; 2011-spherical hinge; 2012-second parallel hinge seat; 2013-first rotation shaft; 2014-third parallel hinge seat; 2016-sixth parallel hinge seat; 2017-fourth parallel hinge seat; 210-uniform strengthening wrist; 211-bracket; 212-motor; 213-motor output shaft screw; 214-sliding shaft; 215-stress adjustment rod; 216-universal locking buckle; 217-fracture reduction needle; 218-sliding-shaft fixing plate; 219-universal locking bayonet fixing shaft; 3-passive manipulator; 301-first spherical hinge; 302-rotary hinge; 303-second spherical hinges; 304-fourth moving member; 305-locking member; 306-first moving member; 307-second moving member; 308-third moving member.

DETAILED DESCRIPTION

In order to make the purpose, technical solutions and advantages of the embodiments of the present invention clearer, the technical solutions in the embodiments of the present invention will be clearly and completely described below in conjunction with the accompanying drawings. Apparently, the described embodiments are some, not all, embodiments of the present invention.

Therefore, the following detailed description of the embodiments of the present invention is not intended to limit the scope of the claimed invention, but merely represents some embodiments of the present invention. Based on the embodiments of the present invention, all other embodiments obtained by persons of ordinary skill in the art without creative efforts fall within the protection scope of the present invention.

It should be noted that, in the case of no conflict, the embodiments of the present invention and the features and technical solutions in the embodiments can be combined with each other.

It should be noted that like numerals and letters denote similar items in the following figures, therefore, once an item is defined in one figure, it does not require further definition and explanation in subsequent figures.

In the description of the present invention, it should be noted that the orientation or positional relationship indicated by the terms "upper", "lower", etc. is based on the orientation or positional relationship shown in the drawings, or the conventionally placed position when the product of the invention is used, or the orientation or positional relationship commonly understood by those skilled in the art, such terms are only for the convenience of describing the present invention and simplifying the description, rather than indicating or implying that the referred device or element must have a specific orientation, be constructed and operative in a particular orientation and therefore are not to be construed as limitations of the invention. In addition, the terms "first", "second", etc. are only used for distinguishing descriptions, and should not be construed as indicating or implying relative importance.

Referring to FIG. 1, an active-passive parallel-connected reduction robot provided in some embodiments includes:

an active manipulator 1 including an active output end with multiple degrees of freedom;

a synchronized motion platform 2, on which a fracture reduction needle is fixedly installed, and the active output end of the active manipulator is connected to the synchronized motion platform; and a passive manipulator 3, of which one end is fixedly arranged, and the other end includes a passive output end having multiple degrees of freedom, and the passive output end is slidably installed on the synchronized motion platform.

The passive manipulator 3 can keep the degree of freedom locked when the active manipulator 1 drives the synchronized motion platform 2 to insert the fracture reduction needle into the fracture end requiring reduction. The active manipulator 1 drives the synchronized motion platform 2 to perform the reduction operation with support of the passive manipulator.

The embodiments proposes an active-passive parallel-connected reduction robot structure: the parallel-connected mechanism of the active manipulator 1 and the passive manipulator 3 is adopted, and the passive manipulator 3 with small volume and large load is arranged in the operation space, and the auxiliary robot is supported by a large rigidity to complete an output of large force load; the active manipulator 1 completes the large power and dexterous movement, and reduces the power demand of the active manipulator 1 with the support of the passive branch chain; the synchronized motion platform 2 outputs the movement of the active manipulator 1 in a crowbar mode to complete the large load and dexterous reduction operation.

Therefore, the active-passive parallel-connected reduction robot structure of the embodiments realizes the fracture reduction operation through the active manipulator 1, the passive manipulator 3 and the synchronized motion platform 2, and is simple, stable, reliable, easy for assemble and unassembled, has a small footprint, and facilitates a surgeon in performing surgical operations.

Further, the active-passive parallel-connected reduction robot of the embodiments includes an active manipulator 1 with six degrees of freedom, a passive manipulator 3 with seven degrees of freedom, and a synchronized motion platform 2 with two synchronous movements.

The active manipulator 1 described in the embodiments can be fixed on the operating trolley or on a permanent support; the active manipulator 1 can actively move according to a route planned before or during the operation; the active manipulator 1 with six degrees of freedom can perform the movement and rotation of the space coordinate system. A movable platform on one end of the synchronized motion platform 2 is fixed on the active manipulator 1, and a movable end on the other end of the synchronized motion platform 2 can move synchronously according to the movable platform fixed on the active manipulator 1. One end of the passive manipulator 3 is fixed on a spherical hinge of the synchronized motion platform 2, and the other end is fixed on the operating bed or a permanent support, or on a trolley; the passive manipulator 3 has seven degrees of freedom, includes two spherical hinges and one rotary hinge, which can be locked passively, serves as motion supports for the synchronized motion platform 2.

The specific implementation is: the active manipulator 1 is fixed on a trolley, or on a permanent support; one end of the synchronized motion platform 2 is installed on the active manipulator 1. One end of the passive manipulator 3 is installed on the operating bed, or can be fixed on the trolley, and the other end is fixed on the spherical hinge of the synchronized motion platform 2, and the spherical hinge can slide on a support rod of the synchronized motion platform 2. When the active manipulator 1 has not reached a predetermined position, it is in a relaxed state, and each joint can move freely. After the active manipulator 1 drives the synchronized motion platform 2 to a predetermined position, the fracture reduction needle is nailed into the fracture end requiring reduction, and the passive manipulator 3 is locked. At this time, the passive manipulator 3 has no degree of freedom, which is equivalent to a rigid fixed support rod. The synchronized motion platform 2 can rotate around its own spherical hinge in three degrees of freedom and slide along the support rod. The active-passive parallel-connected reduction robot can perform a reduction operation at this time, and the passive manipulator 3 provides support for the active manipulator 1 to reduce the load of the active manipulator 1. When the spherical hinge of the synchronized motion platform 2 does not move, the active manipulator 1 drives the synchronized motion platform 2 to move to realize the movement of the fracture end. When the spherical hinge of the synchronized motion platform 2 moves, the synchronized motion platform 2 can rotate around its own spherical hinge in three degrees of freedom and slide along the support bar, and use the spherical hinge to generate a crowbar movement to drive the movement of the fracture end so as to reduce the load of the active manipulator 1.

Figure 2:
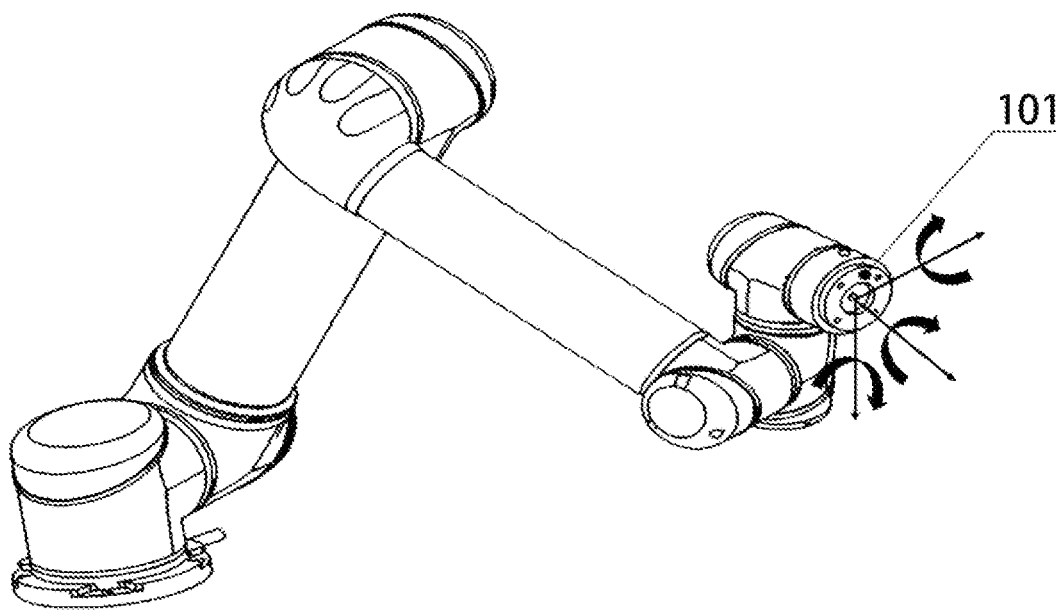
FIG. 2 is a schematic diagram of the three-dimensional structure of the active manipulator of the active-passive parallel-connected robot of the present invention.

As shown in FIG. 2, the active output end of the active manipulator 1 in the embodiments is an end-connection flange 101 with six degrees of freedom in space, which can realize voluntary movement in space posture and provide power for the fracture end reduction operation.

Figure 6:
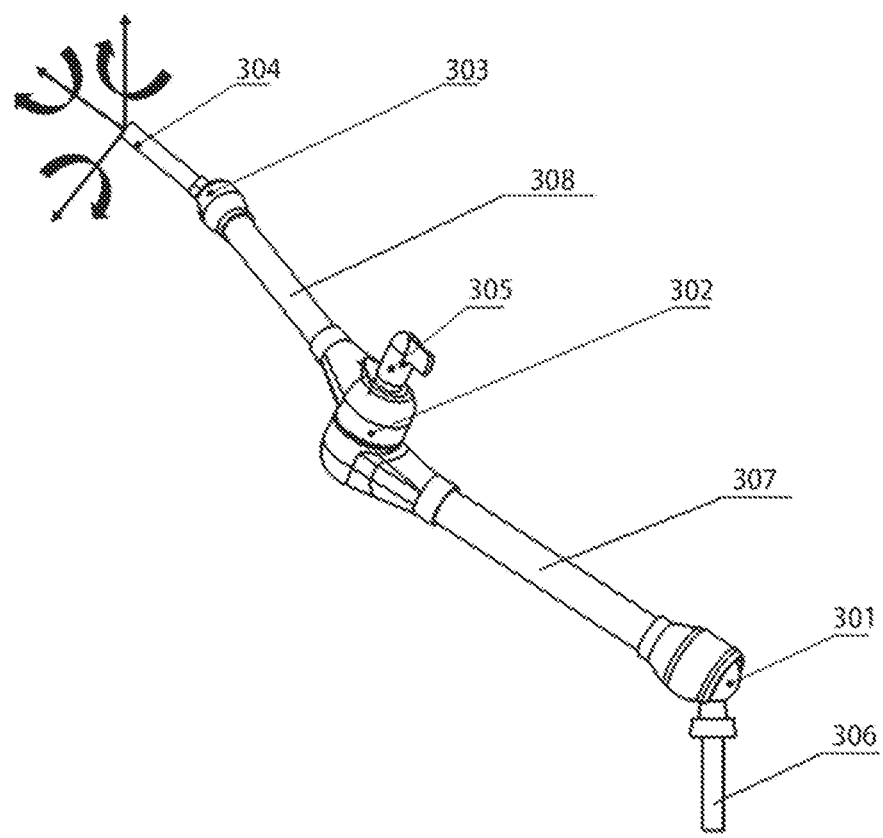
FIG. 6 is a schematic diagram of the three-dimensional structure of the passive manipulator of the active-passive parallel-connected reduction robot of the present invention.

As shown in FIG. 6, the passive manipulator 3 in the embodiments includes a first moving member 306, a second moving member 307 connected to the first moving member 306 through a first spherical hinge 301, and a third moving member 308 rotatably connected to the second moving member 307 through the rotary hinge 302, a fourth moving member 304 connected to the third moving member 308 through the second spherical hinge 303, and a locking member 305 used for locking the first spherical hinge 301, the rotary hinge 302, and the second spherical hinge 303.

The first spherical hinge 301 and the second spherical hinge 303 of the passive manipulator 3 in the embodiments each have three degrees of freedom of movement around the center of the sphere; the rotary hinge 302 has one degree of freedom of rotation; the fourth movement member 304 has six degrees of freedom in space; when the locking member 305 is in a relaxed state, the first spherical hinge 301, the second spherical hinge 303 and the rotary hinge 302 can move freely, while the fourth moving member 304 has six degrees of freedom in space. When the locking member 305 is in the locked state, the first spherical hinge 301, the second spherical hinge 303 and the rotary hinge 302 are all in the locked state, and the fourth moving member 304 cannot move at the same time, and meanwhile the passive branch chain of seven degree of freedom is also in a locked state, which make the passive manipulator 3 serve as a rigid part.

As an implementation of the embodiments, the locking member 305 includes a transmission link and locking blocks that are in contact with the first spherical hinge 301 and the second spherical hinge 303 respectively, and the transmission link is driven by rotation to drive the locking blocks so that the locking blocks are locked in close contact with the first spherical hinge 301 and the second spherical hinge 303 respectively.

Figure 3:
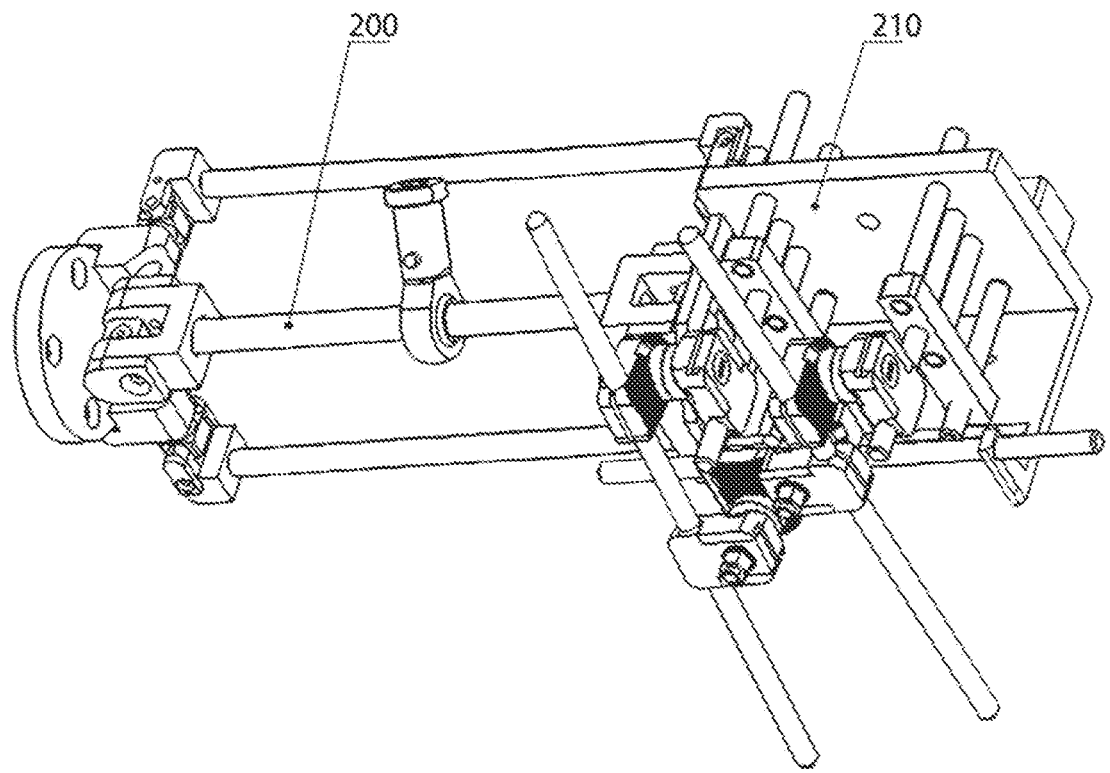
FIG. 3 is a schematic diagram of the three-dimensional structure of the synchronized motion platform of the active-passive parallel-connected reduction robot of the present invention.

As shown in FIG. 3, the synchronized motion platform 2 described in the embodiments includes:
  a platform main body 200 including a robot-end moving platform 201 connected to the active manipulator 1 and a parallel transmission mechanism connected to the robot-end moving platform 201 for power parallel transmission;
  a uniform strengthening wrist 210 being fixedly installed with the fracture reduction needle 217, and the uniform strengthening wrist 210 is fixedly connected with the parallel transmission mechanism of the platform main body 200.

Figure 4:
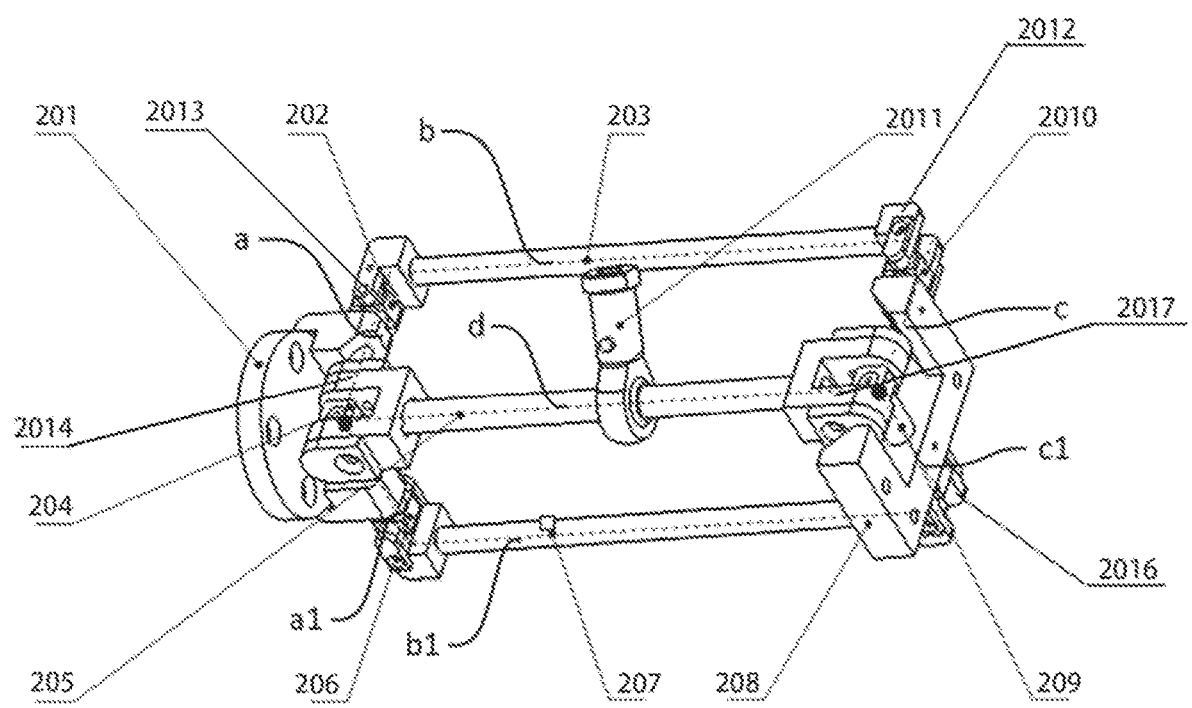
FIG. 4 is a schematic diagram of the three-dimensional structure of the platform main body of the synchronized motion platform of the present invention.

As shown in FIG. 4, the parallel transmission mechanism described in the embodiments includes a first parallel transmission mechanism that performs parallel movement on a first plane and a second parallel transmission mechanism that performs parallel movement on a second plane. The first plane intersects the second plane. The first parallel transmission mechanism and the second parallel transmission mechanism are respectively located in the first plane and the second plane which intersect with each other, so that the follow-up-end moving platform can be kept parallel to the robot-end moving platform in space.

In some embodiments, the parallel transmission mechanism described in the embodiments includes a follow-up end platform 208 fixedly connected with the uniform strengthening wrist 210.

The first parallel transmission mechanism described in the embodiments includes a first support rod 203 and a second support rod 205 parallel to the first support rod 203, a first rotation shaft 2013 and a second rotation shaft 2010 parallel to the first rotation shaft 2013. Both ends of the first support rod 203 are respectively fixedly connected to the first parallel hinge seat 202 and the second parallel hinge seat 2012. One end of the first rotation shaft 2013 is fixedly connected to the robot-end moving platform 201, and the other end is rotatably connected with the first parallel hinge seat 202. One end of the second rotation shaft 2010 is fixedly connected with the follow-up end platform 208, and the other end is rotatably connected with the second parallel hinge seat 2012.

The second parallel mechanism described in the embodiments includes a third support rod 207 parallel to the second support rod 205, a fourth rotation shaft 204 and a fifth rotation shaft 209 parallel to the fourth rotation shaft 204. Both ends of the second support rod 205 are respectively fixedly connected to the third parallel hinge seat 2014 and the fourth parallel hinge seat 2017. Both ends of the third support rod 207 are respectively fixedly connected to the fifth parallel hinge seat 206 and the sixth parallel hinge seat 2016. The fourth rotation shaft 204 rotatably passes through the robot-end moving platform 201, and both ends of the fourth rotation shaft 204 are respectively rotatably installed on the third parallel hinge seat 2014 and the fifth parallel hinge seat 206. The fifth rotation shaft 209 rotatably passes through the follow-up end platform 208, and both ends of the fifth rotation shaft 209 are rotatably installed on the fourth parallel hinge seat 2017 and the sixth parallel hinge seat 2016 respectively.

In some embodiments, the robot-end moving platform 201 described in the embodiments includes a platform body and a first connecting block and a second connecting block which are fixedly connected to the platform body. One end of the first rotation shaft 2013 is fixedly connected to the first connecting block. The fourth rotation shaft 204 rotatably passes through the second connecting block. Optionally, the platform body is a circular connecting flange. The first connecting block and the second connecting block are respectively fixed on the peripheral wall of the circular connecting flange.

In some embodiments, the follow-up end platform described in the embodiments includes a cross arm and a vertical arm fixedly connected to the cross arm. The second rotation shaft 2010 is fixedly connected to the vertical arm, and the fifth rotation shaft 209 rotatably passes through the cross arm. Optionally, the follow-up end platform includes one cross arm and two vertical arms located at both ends of the cross arm, and has a U-shaped structure as a whole.

Here, axis a, axis b, axis c and axis d shown in FIG. 4 constitute the first parallelogram mechanism, and the axis a, and the axis c, the axis b and the axis d will move in parallel in the movement of the first parallelogram mechanism; axis a1, axis b1, axis c1 and the axis d constitute the second parallelogram mechanism, and the axis a1 and axis c1, axis b1 and axis d will move in parallel in the movement of the second parallelogram mechanism. The first parallelogram and the second parallelogram are perpendicular to each other, and the axis a and the axis a1 are perpendicular to each other and intersect at one point, and the axis c and the axis c1 are perpendicular to each other and intersect at one point. The first parallelogram mechanism and the second parallelogram mechanism can realize that the follow-up end moving platform is kept parallel to the robot-end moving platform in space.

Further, the synchronized motion platform 2 described in the embodiments includes a spherical hinge 2011 slidably arranged on the second support rod 205. The passive output end of the passive manipulator 3 is connected to the spherical hinge 2011. The spherical hinge 2011 includes three rotational degrees of freedom around the center of the sphere and is installed on the second support rod 205, and can slide along the second support rod 205. The platform main body 200 can rotate around the spherical hinge 2011, and can also slide along the second support rod 205 to realize the synchronous reduction movement of the space mechanism.

Figure 5:
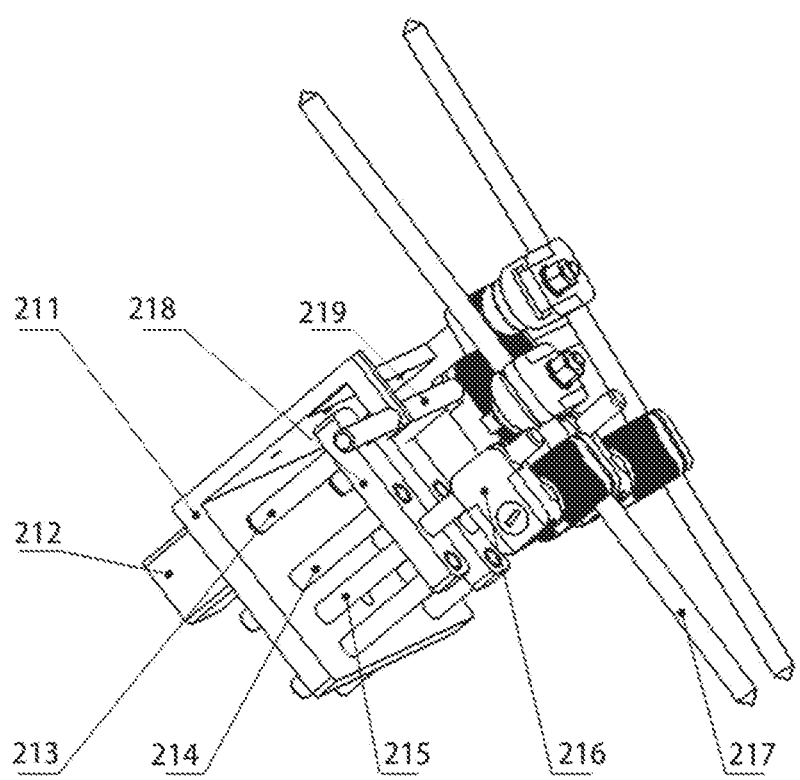
FIG. 5 is a schematic diagram of the three-dimensional structure of the uniform strengthening wrist of the synchronized motion platform of the present invention.

As shown in FIG. 5, the uniform strengthening wrist 210 in the embodiments includes a bracket 211, a motor 212, a motor output shaft screw 213, a sliding shaft 214, a stress adjustment rod 215, a universal locking buckle 216, a fracture reduction needle 217, a sliding-shaft fixing plate 218 and a universal locking bayonet fixing shaft 219.

The motor 212 is fixed on the bracket 211, and the motor output shaft screw rod 213 is fixed on the motor output shaft. The motor output shaft screw rod 213 and sliding-shaft fixing plate 218 are screw driven. The rotation of the motor 212 can drive the sliding-shaft fixing plate 218 to move up and down. The sliding shaft 214 is fixedly connected with the sliding-shaft fixing plate 218. The stress adjustment rod 215 is fixedly connected with the bracket 211. One end of the universal locking buckle 216 is connected together with the fracture reduction needle 217, the other end of the universal locking buckle 216 is connected with the stress adjustment rod 215 or the universal locking bayonet fixing shaft 219. When the universal locking buckle 216 is in a relaxed state, buckles at both ends of the universal locking buckle 216 can move freely, and the buckles at both ends of the universal locking buckle 216 are relatively fixed after locking. When the fracture reduction needle 217 is inserted in the fracture reduction end, the universal locking buckle 216 connects the fracture reduction needle 217 with a racket section, and the motor 212 rotates to drive the sliding-shaft fixing plate 218 to move up and down to adjust moment arms of the stress adjustment rod 215 and the bracket 211, to prevent situations such as secondary fractures caused by the excessive stress of the fracture reduction needle 217 and the fracture reduction end.

In some embodiments, the bracket 211 of the embodiments is an L-shaped bracket. The uniform strengthening wrist of the embodiments includes two sets of fracture reduction needles 217 and corresponding clamping-fixing-adjusting mechanisms.

The above embodiments are only used to illustrate the present invention and are not intended to limit the technical solutions described in the present invention. Although the specification has described the present invention in detail with reference to the above-mentioned embodiments, the present invention is not limited to the above-mentioned specific implementation methods, so any modifications or equivalent replacements to the present invention, and all technical solutions and improvements that do not depart from the spirit and scope of the invention are covered by the scope of the claims of the present invention.

What is claimed is:

1. An active-passive parallel-connected reduction robot comprising:
    an active manipulator provided with an active output of multiple degrees of freedom;
    a synchronized motion platform, on which a fracture reduction needle is fixedly installed, and the active output end of the active manipulator is connected to the synchronized motion platform; and
    a passive manipulator, of which one end is fixed, and the other end comprising a one end of multiple degrees of freedom, and the passive output end is slidably installed on the synchronized motion platform;
    the passive manipulator keeps degrees of freedom locked in response to the active manipulator drives the synchronized motion platform to insert the fracture reduction needle into a fracture end requiring reduction, and the active manipulator drives the synchronized motion platform to perform a reduction operation under the support of the passive manipulator.

2. The active-passive parallel-connected reduction robot according to claim 1, wherein the synchronized motion platform comprises:
    a platform main body comprising a robot-end moving platform connected with the active manipulator and a parallel transmission mechanism connected with the robot-end moving platform for parallel transmission of power;
    a uniform strengthening wrist configured to fixedly install the fracture reduction needle, and the uniform strengthening wrist is fixedly connected with the parallel transmission mechanism of the platform main body.

3. The active-passive parallel-connected reduction robot according to claim 2, wherein the parallel transmission mechanism comprises a first parallel transmission mechanism that performs a parallel motion on a first plane and a second parallel transmission mechanism that performs parallel motion on a second plane, the first plane intersects the second plane.

4. The active-passive parallel-connected reduction robot according to claim 3, wherein the parallel transmission mechanism comprises a follow-up end platform fixedly connected with the uniform strengthening wrist;
    the first parallel transmission mechanism comprises a first support rod and a second support rod parallel to the first support rod, a first rotation shaft and a second rotation shaft parallel to the first rotation shaft, and both ends of the first support rod are respectively fixedly connected to a first parallel hinge seat and a second parallel hinge seat, one end of the first rotation shaft is fixedly connected to the robot-end moving platform, and the other end of the first rotation shaft is rotatably connected to the first parallel hinge seat; one end of the second rotation shaft is fixedly connected to the follow-up end platform, and the other end of the second rotation shaft is rotatably connected to the second parallel hinge seat;
    the second parallel mechanism comprises a third support rod parallel to the second support rod, a fourth rotation shaft and a fifth rotation shaft parallel to the fourth rotation shaft; both ends of the second support rod are respectively fixedly connected to a third parallel hinge seat and a fourth parallel hinge seat; both ends of the third support rod are respectively fixedly connected to a fifth parallel hinge seat and a sixth parallel hinge seat; the fourth rotation shaft rotatably passes through the robot-end moving platform, and both ends of the fourth rotation shaft are rotatably installed on the third parallel hinge seat and the fourth parallel hinge seat respectively; the fifth rotation shaft rotatably passes through the follow-up end platform, and both ends of the fifth rotation shaft are respectively rotatably installed on the fourth parallel hinge seat, and the sixth parallel hinge seat.

5. The active-passive parallel-connected reduction robot according to claim 4, wherein the robot-end moving platform comprises a platform body and a first connecting block and a second connecting block fixedly connected to the platform body; one end of the first rotation shaft is fixedly connected with the first connecting block; the fourth rotation shaft rotatably passes through the second connecting block.

6. The active-passive parallel-connected reduction robot according to claim 4, wherein the follow-up end platform comprises a cross arm and a vertical arm fixedly connected with the cross arm; the second rotation shaft is fixedly connected to the vertical arm, the fifth rotation shaft rotatably passes through the cross arm.

7. The active-passive parallel-connected reduction robot according to claim 4, wherein the synchronized motion platform comprises a spherical hinge slidably arranged on the second support rod, and the passive output end of the passive manipulator is connected to the spherical hinge.

8. The active-passive parallel-connected reduction robot according to claim 2, wherein the uniform strengthening wrist comprises a bracket, a motor, a motor output shaft screw, a sliding shaft, a stress adjustment rod, a universal locking buckle, a sliding shaft fixed plate and a universal locking bayonet fixed shaft;
    wherein the motor is fixed on the bracket, the motor output shaft screw is fixed on the motor output shaft, the motor output shaft screw and the sliding-shaft fixing plate are screw driven; a rotation of the motor drives the sliding-shaft fixing plate to move up and down; the sliding shaft is fixedly connected with the sliding-shaft fixing plate; the stress adjustment rod is fixedly connected with the bracket; one end of the universal locking buckle is connected with the fracture reduction needle, and the other end of the universal locking buckle is fixed with the stress adjustment rod or the universal locking bayonet fixed shaft;
    in response to the fracture reduction needle being inserted into the fracture reduction end, the universal locking buckle fixes the fracture reduction needle and a racket section together; the motor rotates to drive the sliding shaft fixed plate to move up and down to adjust arm of force of the stress adjustment rod and the bracket.

9. The active-passive parallel-connected reduction robot according to claim 1, wherein the active output end of the active manipulator is an end-connection flange with six degrees of freedom in space.

10. The active-passive parallel-connected reduction robot according to claim 1, wherein the passive manipulator comprises a first moving member, a second moving member connected to the first moving member through a first spherical hinge, and a third moving member rotatably connected to the second moving member through a rotary hinge, a fourth moving member connected to the third moving member through a second spherical hinge, and a locking member for locking the first spherical hinge, the rotary hinge, and the second spherical hinge.

\* \* \* \* \*